United States Patent [19]

Stebbing et al.

[11] 4,151,350

[45] Apr. 24, 1979

[54] POLY-5-HYDROXYCYTIDYLIC ACID COPOLYMERS

[75] Inventors: Nowell Stebbing, High Wycombe; Michael A. Eaton, Bledlow, both of England

[73] Assignee: G. D. Searle & Co., Skokie, Ill.

[21] Appl. No.: 857,851

[22] Filed: Dec. 5, 1977

[30] Foreign Application Priority Data

Dec. 23, 1976 [GB] United Kingdom ............... 53822/76

[51] Int. Cl.$^2$ ..................... C07H 17/00; A61K 31/70
[52] U.S. Cl. ........................ 536/29; 536/28; 536/27; 424/180
[58] Field of Search ............... 536/29, 28, 23

[56] References Cited

U.S. PATENT DOCUMENTS 3,935,185  1/1976  Hutchinson et al. ............... 536/29

FOREIGN PATENT DOCUMENTS 51-8295  1/1976  Japan ............................ 536/23

OTHER PUBLICATIONS

Means, G., et al., Biochem. Biophys. Acta, 247, 441 (1971).
Eaton, M., et al., Biochem. Biophys. Acta, 349, 281 (1973).

*Primary Examiner*—Johnnie R. Brown
*Assistant Examiner*—Blondel Hazel
*Attorney, Agent, or Firm*—John J. McDonnell; Michael T. Murphy

[57] ABSTRACT

The invention relates to copolymers of 5-hydroxycytidylic acid and at least one other polynucleotide selected from cytidylic acid and monomers derived therefrom by bromination. The polymers of the invention are prepared by the bromination of polycytidylic acid and subsequent hydrolysis of the product. The copolymers of the invention demonstrate antiviral properties in vivo.

4 Claims, No Drawings

POLY-5-HYDROXYCYTIDYLIC ACID COPOLYMERS

The present invention relates to copolymers comprising 5-hydroxycytidylic acid and having antiviral properties.

The present invention encompasses copolymers comprising:

(a) 35–95% of 5-hydroxycytidylic acid monomer residue,
(b) 0–40% of 5-bromocytidylic acid monomer residues, and
(c) 0–65% of cytidylic acid or other nucleotide monomer residues derived from bromination of polycytidylic acid; the percentages being molar percentages based on the total monomer wherein at least one of (b) or (c) is present to about 5% and the copolymer having an $S_{W,20}$ value of 3 to 13.5.

Preferred copolymers are in the range

| a) 50–95% | a) 35–95% |
| b) 14–40% | b) 0–40% |
| c) 0–25% | c) 5–65% | wherein (a), (b), and (c) represent the above described entities.

The reference above to (b) 5-bromocytidylic acid monomer residue is to be understood to include not only 5-bromocytidylic acid but bromination derivatives of cytidylic acid having an ultra-violet absorbance spectrum corresponding substantially to that for 5-bromocytidylic acid and showing similar chromatographic behaviour.

As stated above the percentage proportions of the monomer constituents of the copolymer are expressed as molar percentages based on the total monomer. These values are arrived at by the analysis of the copolymer by hydrolysis with sodium hydroxide followed by thin layer chromatography and the separated components are quantitated by scintillation counting (where radio labelled poly 5-hydroxycytidylic acid was used in the preparation of the copolymer) or by phosphate analysis. This method of analysis gives therefore an expression of the molar percentage values of the monomers relative to each other and not an absolute value of the components.

Since the copolymer can not readily be obtained in absolutely pure form, e.g. it normally contains water and inorganic salt impurities, these relative values differ to some extent from the absolute values for the same component from the same batch, i.e. the value for example for the 5-hydroxycytidylic acid based on the total copolymer weight including unavoidable impurities. This absolute value can be acertained by an alternative analysis method as follows:

The copolymer is hydrolysed with sodium hydroxide and the product subjected to high pressure liquid chromatography (HPLC). This method produces good separation of the components. The amount of each separated component obtained from a given weight of copolymer is calculated by comparison of peak areas (on HPLC trace) with those given by a known weight of each monomeric component. This method therefore gives an absolute value, i.e. a weight percentage based on the total copolymer weight, including impurities, for each identifiable component.

Using this alternative analysis method the copolymer of the invention can be defined as a copolymer having an $S_{W,20}$ value of from 3 to 13.5 and comprising from 30 to 95% by weight, based on the total copolymer weight (absolute value), of 5-hydroxycytidylic acid monomer, the balance of the monomers being cytidylic acid, and/or monomers derived therefrom by bromination, and unavoidable impurities, for example water and inorganic salts.

A preferred polymer analyzed by this procedure contains 38.5% by weight, based on the total copolymer weight, of 5-hydroxycytidylic acid monomer. The same copolymer, analysed by the method of hydrolysis, thin layer chromatography and subsequent quantification, comprised 51 molar percent 5-hydroxycytidylic acid; 29 molar percent cytidylic acid and 19 molar percent 5-bromocytidylic acid.

The present invention also encompasses pharmaceutical compositions comprising the above copolymers in combination with polyinosinic acid (poly I) in an injectable or oral pharmaceutical carrier wherein the sum of $S_{20,W}$ of poly I and the above copolymers is more than 12. Preferred copolymers are those having the following respective molar percentages, based on the total monomer weight, of (a) 5-hydroxycytidylic acid monomer residues (b) 5-bromocytidylic acid monomer residues and (c) cytidylic acid of other nucleotide monomer residues,

| (a) 50% | (a) 81% | (a) 60–62% |
| (b) 25% | (b) 19% | (b) 14–16% |
| (c) 25% |         | (c) 24–26% | characteristically copolymers of the present invention having 35–95 molar percent 5-hydroxycytidylic acid residues, based on the total monomer weight, and a molecular weight of about 100,000.

Thus, the present invention encompasses a copolymer prepared by the process of brominating polycytidylic acid at pH 2.5–8.0, removing excess bromine, and hydrolysing the bromine substituted polymer at a basic pH, said copolymer characterized as having 35–95 molar percent 5-hydroxycytidylic monomer residues.

The 5-hydroxycytidylic acid monomer residue has the formula:

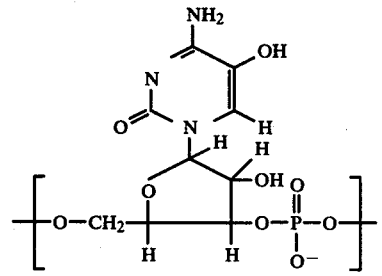

and it and its 3' phosphate isomer comprise the main building unit of the polymers of the present invention.

Copolymers of the present invention are preferably made by brominating polycytidylic acid (poly C) and then hydrolysing the resulting bromide by modifications of the methods of Means and Fraenkel-Conrat, Biochim, Biophys. Acta 247, 441 (1971). Bromine water is added to poly C dissolved in water or saline at a concentration up to saturation at 0°–10° C. and the pH held at 2.5–8.0. The bromine group is hydrolyzed at basic pH to the 5-hydroxycytidylate. Maximum bromination and subsequent hydroxylation is obtained when the solution just turns yellow and a bromine scavenger is then added until the solution is colourless. Addition of smaller amounts of bromine water results in lower percentages of bromination and 5-hydroxycytidylate monomer residues in the product upon hydrolysis. After addition of a bromine scavenging agent the solution is adjusted to basic pH at a temperature between 0° and 50° and after 1-24 hours the product is pumped through 2 Biofibre 50 beakers (Biorad Laboratories). The polymer is lyophilized or frozen at $-20°$ C. alone or in the presence of salt. The polymer forms a gel if frozen alone but the presence of salt prevents gelling.

Thus, polycytidylic acids having $S_{20,w}$ values of 13.2, 10.5, 8.29, 5.94, 3.88, 3.08 are brominated and the resulting bromide hydrolysed under controlled conditions to provide copolymers of the present invention. These copolymers, although they contain residues other than 5-hydroxycytidylic acid, are hereafter generally referred to simply as poly ho$^5$C.

The procedure for preparing compounds of the present invention are summarized as follows:

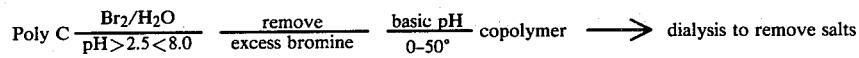

Compounds of the present invention are useful by virtue of their antiviral activity. The 5-hydroxycytidylic acid containing copolymers have anti-viral activity alone or, preferably, when mixed with polyinosinic acid and such formulations have low toxicity compared with other antiviral polynucleotide preparations.

Thus, doses in the order of 1 mg/kg of polyinosinic acid (poly I) and 1 mg/kg of copolymers of the present invention intraperitoneally in a suitable pharmaceutical carrier administered 4-10 hours before infection serve as an effective prophylactic antiviral treatment. Those skilled in the pharmaceutical arts will recognise a variety of formulations and routes of administration. Doses will vary with individuals being treated, formulation and route of administration. Multiple doses before and/or after infection will also be used in treating various infections.

Means and Fraenkel-Conrat, Biochim. Biophys. Acta 247, 441-448 (1971) describe poly C/5-hydroxycytidylate containing 15% 5-hydroxycytidylate residues. Halopolynucleotides are disclosed by Means and Fraenkel-Conrat above and also in British Pat. No. 1,295,684, as well as De Clerq et al. Ann. N.Y. Acad. Sci. 173, 444-461 (1970). Poly-(5-hydroxycytidylic acid), homopolymer, is described by Eaton and Hutchinson, Biochim. Biophys. Acta. 319, 281-287 (1973). The present invention is particularly distinct in that it encompasses copolymers having between 35 and 95 molar percent 5-hydroxycytidylic acid monomer residues, based on the total monomer.

The hereinafter set out examples are intended as illustrations of the present invention and should not be construed as a limitation of the invention in spirit or scope.

EXAMPLE 1

5 gms of polycytidylic acid (sodium salt) is dissolved in 300 mls sterile water and the pH adjusted to 5.5 at 0°-10° C. To the stirred viscous solution at 0°-10° C. is added saturated bromine water (pH 5.5) at a rate of 300 mls/hr maintaining the pH at 5.5 by adding 1 M NaOH with a pH stat. After approximately 600 mls bromine water have been added the reaction turns pale yellow (i.e. free bromine in solution) and the bromination reaction is terminated by the addition of a few mls of 10% cytidine solution. The solution turns colourless. Up to this point the pH-stat has dispensed 12.7 mls 1 M NaOH. The pH of the reaction is now increased to 9.5 and the temperature increased to 37° C. The pH of the reaction is maintained at 9.5 by the addition of 1 M NaOH. Alkali is rapidly consumed at first but after 1 hour the reaction has slowed down and after 2 hours the reaction is complete. A further 12.3 mls of 1 M NaOH are required.

The polymer solution is now cooled to 0°-10° C. and excess salt and low molecular weight impurities removed by dialysis. The polymer solution (final volume approximately 900 mls) is pumped through two Biofibre 50 beakers (Biorad Laboratories) over 12 hours. The salt free polymer is lyophilized.

The polymer prepared above has a molecular weight approximated the same as the molecular weight of the polycytidylic acid used as starting material, i.e. no break-down of the chain occurs. The molecular weight is typically around 100,000 by comparison with standards on 3% polyacrylamide gels.

The ultraviolet spectrum of the polymer shows two maxima 290 nm and 228 nm. There is a minimum at 264 nm.

The polymer is hydrolysed by pancreatic ribonuclease at a slow rate at pH 6.5, 15% hypochromicity being released. Hypochromicity is defined a $$\frac{\text{A MONOMER} - \text{A POLYMER}}{\text{A MONOMER}}$$

On exhaustive hydrolysis with pancreatic ribonuclease (1 mg/ml 24 hrs. at 37° C.) the polymer is essentially degraded to monomers. The polymer composition can be analysed by chromatography on cellulose TLC plates. The plate is eluted with 1 M ammonium acetate, pH 9.0/ethanol (1:1, V/V). The Rf's of br$^5$CMP and ho$^5$CMP in this system are 0.45 and 0.36. If this experiment is carried out with $^{14}$C-labelled polycytidylic acid the % composition of the polymer can easily be determined by cutting out the bands and counting them in a scintillation counter. The % of the total counts migrating with ho$^5$CMP is 61%, 14 Br$^5$CMP, and 25% polycytidylic acid monomer and other reaction products which result from the bromination of polycytidylic acid and its subsequent hydrolysis.

The nucleoside monophosphates can be eluted from the TLC plate and their spectra determined. The ho$^5$CMP (Rf=0.30) has a λ max at 292 nm and at 227. The spectrum has a λ min at 264 nm.

The br$^5$CMP (Rf=0.45) has λ max at 288 nm and 222 nm. The spectrum has a λ min at 264 nm.

EXAMPLE 2

106 mg of polycytidylic acid (lithium salt) is dissolved in 45 mls citrate buffer (0.05 M; pH 7.0) and cooled to 4° C. To the stirred viscous solution at 4° C. is added saturated bromine-water at a rate of 60 mls/hr. After approximately 12 ml bromine-water have been added, the reaction mixture takes on a yellow tinge; this is the end-point. Excess bromine is destroyed by the addition of approximately 100 ml cyclohexene. The pH of the solution is now increased to 9.5 and maintained at this value by the addition of 0.1 M NaOH from a pH stat. Simultaneously, the temperature of the reaction mixture is increased to 37° C. After 3 hours the consumption of alkali has ceased and the reaction is complete.

The polymer solution is now cooled to 4° C. and buffer, salt and other low molecular-weight impurities are removed by dialysis in cellulose-acetate tubing against distilled water (6 changes of 5l each); during this process, the volume of the polymer solution increases by approximately 50%, and the final solution volume is approximately 100 ml.

The polymer prepared above has a molecular weight approximately the same as that of the polycytidylic acid starting material, and is typically around 100,000 by comparison with standards on 3% polyacrylamide gels.

The ultraviolet spectrum of the polymer at pH 7.0 shows two maxima at 290 nm and 228 nm and a minimum at 264 nm; at pH 11 the longer-wavelength maximum is at 320 nm with a minimum at 273 nm.

On alkaline hydrolysis at 37° C. in 0.5 M NaOH for 4 h., the polymer is degraded to 2' and 3' mononucleotides which can be analysed by TLC as described in EXAMPLE ONE. If this experiment is carried out with $^{14}C$-labelled polycytidylic acid the % of the total counts migrating with ho$^5$CMP (mixed 2' and 3' isomers) is 63%; 0% Br$^5$CMP, and 37% CMP and related nucleotide monomer residues.

EXAMPLE 3

Encephalomyocarditis (EMC) virus is administered intraperitoneally in 0.1 ml to female albino mice 6 to 8 weeks old and weighing 18 to 21 gm.

Polyriboinosinic acid (poly I) with sedimentation values ($S_{20,W}$) of 12.5, 10.6, 7.94, 6.13, 4.39 and 2.5 and polyribocytidylic acid (poly C) with sedimentation values of 13.2, 10.5, 8.29, 5.94, 3.88 and 3.08 were from P-L Biochemicals, Milwaukee, U.S.A.

The various poly C preparations were converted to copolymers containing 5-hydroxycytidylic acid residues by treatment with bromine water as described in Example 1. This method produces copolymers containing residues of ho$^5$CMP and br$^5$CMP. The copolymers are here referred to simply as poly(5-hydroxycytidylic acid), (poly ho$^5$C) and the various preparations contain between 58% and 62% 5-hydroxycytidylic acid (ho$^5$CMP)residues and the remainder Br$^5$CMP. The poly ho$^5$C preparations are analysed on 3.0% and 7.5% polyacrylamide gels with sodium dodecyl sulphate in the running buffer, Loening, Biochem. J. 113, 131–138, and no changes are detected in the sizes of the various preparations as a result of the bromine water treatment. Sodium chloride is added to the poly ho$^5$C preparations before lyophilization and redissolving them to avoid gelling of the product. All polynucleotides are finally made up to 0.89% (w/v) NaCl, 10 mM HEPES, pH 7.5 (HBS) and administered intraperitoneally in a volume of 0.1 ml.

The survival time (t) of mice in hours is obtained from records prepared twice daily. An average survival time for a group of mice is obtained by calculating the mean of the reciprocals of the survival times taking the reciprocal of survivors to be zero and multiplying this mean by 100. These calculations are carried out on the data at 18 days post-infection by which time no further deaths occur and the values obtained are designated as values of $1/t \times 10^2$. Since mice infected with more than $1 \times LD_{100}$ of the virus all die around 100 hours after infection the $1/t \times 10^2$ values for infected control groups is around 1.00. Where treatment of mice causes some to survive and/or delays the time of death the $1/t \times 10^2$ value is lower. Values of $1/t \times 10^2$ are used here as comparative measures of the survival of different groups of mice. However, significant differences in the survival times of different groups of mice are tested for by calculating $X^2$ values by the log-rank method of Peto and Pike, Biometrics 29, 579 (1973) on the survival data up to 18 days post-infection. The significance level of the $X^2$ vlaues, which have one degree of freedom are indicated by asterisks as follows: * $p<0.001$; , $p<0.01$; *, $p<0.05$. No asterisk indicates $p>0.05$ and is taken as non-significant. Significance (p=0.05) is reached at $X^2$ values of 3.84.

The data in Table 1 shows that mixtures of poly I and poly ho$^5$C in which the poly ho$^5$C component has an $S_{20,W}$ value of 8.29 or greater confer significant protection regardless of the size of the poly I component when administered intraperitoneally 6 hours before infection with EMC virus. Logrank $X^2$ comparisons between all these treatments show some differences, significant at p=0.03 in the largest case. Using poly ho$^5$C with an $S_{20,W}$ value below 8.29, significant protection is only achieved with mixtures containing the larger sizes of poly I. Moreover this effect becomes more pronounced as the size of poly ho$^5$C decreases: at $S_{20,W}$ values of 5.94, 3.88 and 3.08 only the 4 largest, 2 largest and one largest size of poly I are significantly protective, respectively.

EXAMPLE 4

EMC virus is administered to female albino mice as described in Example 3 and the protective effect of administering various polynucleotides is analysed as described in Example 3.

Unfractionated poly I and poly C were obtained from P-L Biochemicals and these had mean sedimentation values of 9.43 and 10.0 respectively. The poly C is treated with bromine water as described in Example 1 to produce copolymers containing 81% ho$^5$CMP, 19% Br$^5$CMP or 62% CMP and 38% Br$^5$CMP. The first of these preparations was frozen in the absence of salt and a gelled material is obtained on thawing. This material, alone or mixed with poly I can be administered intraperitoneally to mice trhough a wide-bore hypodermic syringe. The second of the poly ho$^5$C preparations is stored frozen in the presence of 0.89% (w/v) sodium chloride and this preparation is soluble when thawed.

These poly ho$^5$C preparations alone, or mixed with equal weights of poly I confer protection against EMC virus infection of mice, as indicated by the data in Table 2.

EXAMPLE 5

EMC virus is administered to female albino mice as described in example 3 and the protective effect of administering various polynucleotides is analysed as described in example 3. Poly I and poly C, as described in example 4, are used and the poly C converted to poly ho$^5$C also as described in example 4 and this gives a copolymer containing 60% ho$^5$CMP, 38% br$^5$CMP and 2% CMP. This poly ho$^5$C preparation is frozen in the absence of salt and gives a gelled material on thawing. This material is mixed with an equal weight of poly I and administered intraperitoneally to mice through a wide bore hypodermic syringe.

The mixture of poly I and poly ho$^5$C is administered in doses of 50 μg of 200 μg/mouse 6 hours before intraperitoneal or intravenous infection with EMC virus doses of 1, 10 and 100×LD$_{100}$. Protection against these infections is observed in all cases as shown by the data in Table 3. These results show that the polynucleotide preparations need not be administered by the same route as the virus in order to show anti-viral effects.

EXAMPLE 6

Mixtures containing equal weights of poly I and poly ho$^5$C are administered to 6 week old female albino mice with mean weight of 23 g. The toxicity of these mixtures (LD$_{50}$) are compared with the toxicity of poly I alone and the double-stranded complex between poly I and poly C (poly I:C). The mixtures contained poly ho$^5$C containing 62% ho$^5$CMP and 38% br$^5$CMP obtained by bromine water treatment of poly C as described in example 1. Some of this material was frozen in the absence of salt to produce a gelled material when thawed. This material was homogenised and mixed with an equal weight of poly I and then administered intraperitoneally to the mice. Some of the poly ho$^5$C is kept unfrozen and mixed with poly I and then administered intraperitoneally to the mice. The data in Table 4 show that the LD$_{50}$ values for the mixtures of poly I and poly ho$^5$C are considerably higher than for poly I:C. Thus our mixtures of poly I and poly ho$^5$C have considerable advantage over poly I:C which is known to have anti-viral effects particularly by virtue of its ability to induce interferon.

EXAMPLE 7

To test the efficacy of poly ho$^5$C-copolymer against a primate virus infection, the combined effect of poly I and poly ho$^5$C-copolymer was examined in rhesus monkeys six hours before infection with the avirulent FN strain of Yellow Fever Virus. A single treatment was given to one monkey at a total polynucleotide dose of 20 mg/kg and plasma antibody titres determined at 7, 10 and 14 days post infection by determining the plasma dilutions given 50% inhibition of plaque formation of the virus in monolayer cultures of Vero-cells. The result, in the table, shows that at all 3 times the antibody level was greatly reduced as a result of treatment with the polynucleotide material.

TABLE

Effect of a mixture of poly I and poly ho$^5$C-copolymer on plasma antibody titres to Yellow Fever Virus.

| Treatment i.v. 6h before infection | Plasma dilutions giving 50% p.f.u. inhibition of 7, 10 and 14 days post-infection | | |
|---|---|---|---|
| | 7 day | 10 day | 14 day |
| Saline | 100 | 1,380 | >2,000 |
| M | 30 | 142 | 174 |

Both monkeys (adult males) vaccinated i.m. with 1,000 mouse LD$_{50}$ units of FN strain Yellow Fever Virus 6h after treatments.
Saline = 2 ml/kg body weight 0.8% NaCl.
M = A mixture containing equal weights of poly I and poly ho$^5$C-copolymer at a total polynucleotide conc TABLE 3-continued The protective effect of 50μg and 200μg of a mixture of poly I and poly ho⁵C 6h before intraperitoneal or intravenous infection with EMC virus doses of 1, 10 and 100 × LD₁₀₀

Values of $1/t \times 10^2$ and logrank $X^2$ comparisons with the infected controls shown in brackets

| Route of Infection | Amount of the mixture administered 6h before infection | | Infected Controls | |
|---|---|---|---|---|
| | 50 μg | 200 μg | $1/t \times 10^2$ | $LD_{100}$ |
| i.v. | 0.24 (15.63***) | 0.12 (17.39***) | 0.98 | |

Number of mice per group = 15
I.p. = intraperitoneal, i.v. = intravenous

TABLE 4

Acute toxicity of an intraperitoneally administered mixture of poly I and poly ho⁵C compared with poly I and poly I:C

| Polynucleotides administered | Survival of mice per group Total mg polynucleotides administered | | | | | | | | Estimated $LD_{50}$ dose | |
|---|---|---|---|---|---|---|---|---|---|---|
| | 0.5 | 0.8 | 1.0 | 1.3 | 8 | 12 | 16 | 24 | mg/mouse | mg/kilogram |
| poly I:C | 10/10 | 8/10 | 6/10 | 0/10 | — | — | — | — | 1.1 | 48 |
| poly I | — | — | — | — | 5/6 | 5/6 | 3/6 | 1/6 | 16 | 695 |
| poly I, poly ho⁵C (gelled) | — | — | — | — | 4/6 | 3/6 | 4/6 | 2/6 | 12 | 521 |
| poly I, poly ho⁵C (soluble) | — | — | — | — | 5/6 | 5/6 | 5/6 | 4/6 | >24 | 1044 |

Poly I:C was made up in HBS at 5mg, 8mg, 10mgs and 13mg/ml and 0.1ml injected per mouse to give the total doses shown.
Poly I was made up in HBS at 12mg/ml and appropriate volumes administered to give the final doses indicated.
The mixtures of equal weights of poly I and poly ho⁵C were made up in HBS to a total polynucleotide concentration of 12mg/ml and appropriate volumes administered to give the final doses indicated.
No deaths occurred after 7 days (records maintained 2 months) and mean time of death was 35h.

What is claimed is:

1. A copolymer having an $S_{W,20}$ value of from 3 to 13.5 and comprising essentially from 30 to 95% by weight, based on the total copolymer weight, of 5-hydroxycytidylic acid monomer, the balance being cytidylic acid, and/or monomers derived therefrom by bromination, there being at least 5% by weight, based on the total copolymer weight, of the cytidylic acid and/or bromination derivatives thereof.

2. A copolymer as claimed in claim 1 comprising (a) from 50 to 95 percent of 5-hydroxycytidylic acid monomer, (b) from 14 to 40 molar percent of a brominated monomer derived from cytidylic acid and having an ultra-violet absorbance spectrum corresponding substantially to 5-bromocytidylic acid and showing similar chromagraphic behavior and (c) from 0 to 25 molar percent of cytidylic acid and/or monomers derived therefrom, and wherein the copolymer comprises at least 5 molar percent of (b) and/or (c), the percentages being based on the total monomer.

3. A copolymer as claimed in claim 1 comprising (a) from 35 to 95 molar percent of 5-hydroxycytidylic acid monomer, (b) from 0 to 40 molar percent of a brominated monomer derived from cytidylic acid and having an ultraviolet absorbance spectrum corresponding substantially to a 5-bromocytidylic acid and showing similar chromagraphic behavior and (c) from 5 to 65 molar percent of cytidylic acid and/or monomers derived therefrom, and wherein the copolymer comprises at least 5 molar percent of (b) and/or (c), the percentages being based on the total monomer.

4. A copolymer as claimed in claim 1 comprising (a) 51 molar percent of 5-hydroxycytidylic acid monomer, (b) 19 molar percent of a brominated monomer derived from cytidylic acid and having an ultra-violet absorbance spectrum corresponding substantially to a 5-bromocytidylic acid and showing similar chromagraphic behavior and (c) 29 molar percent of cytidylic acid and/or monomers derived therefrom, the percentages being based on the total monomer.

* * * * *